(12) United States Patent
Wong et al.

(10) Patent No.: US 6,620,356 B1
(45) Date of Patent: Sep. 16, 2003

(54) POROUS CONSTRUCTS FABRICATED BY GAS INDUCED PHASE INVERSION

(75) Inventors: Betty Wong, San Diego, CA (US); John E. Kemnitzer, San Diego, CA (US)

(73) Assignee: Integra LifeSciences Corp., Plainsboro, NJ (US)

( * ) Notice: Subject to any disclaimer, the term of this patent is extended or adjusted under 35 U.S.C. 154(b) by 0 days.

(21) Appl. No.: 09/836,089

(22) Filed: Apr. 17, 2001

Related U.S. Application Data
(60) Provisional application No. 60/198,026, filed on Apr. 18, 2000.

(51) Int. Cl.$^7$ ............................................... B29C 65/00
(52) U.S. Cl. ..................... 264/41; 210/500.27; 210/490; 264/83; 521/51; 521/64; 521/155
(58) Field of Search ...................... 210/500.27, 500.29, 210/490; 264/41, 83; 521/51, 64, 155

(56) References Cited

U.S. PATENT DOCUMENTS

| | | |
|---|---|---|
| 4,946,940 A | 8/1990 | Guckes et al. |
| 5,066,684 A | 11/1991 | LeMay |
| 5,116,883 A | 5/1992 | LeMay |
| 5,158,986 A | 10/1992 | Cha et al. |
| 5,181,940 A * | 1/1993 | Bikson et al. |
| 5,229,045 A * | 7/1993 | Soldani |
| 5,360,478 A | 11/1994 | Krukonis et al. |
| 5,387,621 A * | 2/1995 | Soldani |
| 5,389,263 A | 2/1995 | Gallagher et al. |
| 5,422,377 A | 6/1995 | Aubert |
| 5,708,040 A * | 1/1998 | Hong et al. |
| 5,864,923 A | 2/1999 | Rouanet et al. |

OTHER PUBLICATIONS

Bourke et al., "Effects of Static and Cyclic Loading in Different Environments on the Strength Retention of Resorbable Synthetic Polymer Fiber Scaffolds", *Soc. Biomater. 25th Ann. Mtg. Trans.* 1999 222.

Brode et al., "Biosmart ® Tyrosine Polycarbonates", *Polymer Preprints, Am. Chem. Soc., Div. Polym. Chem.* 1998 39:230–231.

Chiou et. al., "Plasticization of Glassy Polymers by $CO_2$", *J. Appl. Polym. Sci.* 1985 30:2633–2642.

Cohen et. al. "Pore generation in asymmetric polymeric membranes—Correlation with solvent mobilities", *Polymer Bulletin* 1999 42:345–352.

Craig et al., "Concept and Progress in the Development of RGD–Containing Peptide Pharmaceuticals", *Biopolymers (Peptide Science)* 1995 37:157–175.

Freed et al., "Neocartilage formation in vitro and in vivo using cells cultured on synthetic biodegradable polymers", *J. Biomed. Mater. Res.* 1993 27:11–23.

Gante J., "Peptidomimetics–Tailored Enzyme Inhibitors", *Angew. Chem. Int. Ed. Engl.* 1994 33:1699–1720.

Harris et. al., "Open pore biodegradable matrices formed with gas foaming", *Biomed. Mater. Res.* 1998 42:396–402.

Haubner et. al., "Cyclic RGD Peptides Containing β–Turn Mimetics", *J. Am. Chem. Soc.* 1996 118:7881–7891.

Kassim et. al., "The Temperature Dependence of the Solubility of Carbon Dioxide in Several Extraction Solvents" *Fluid Phase Equilibria* 1988 41:287–294.

Kojima J. et. al., "Early Stage Spinodal Decomposition in Polymer Solution under High Pressure", *Macromolecules* 1999 32:1809–1815.

Matsuyama et al., "Membrane Formation via Phase Separation Induced by Penetration of Nonsolvent from Vapor Phase. II. Membrane Morphology" *J. of Appl. Polymer Sci.* 1999 74:171–178.

Nam et al., "Porous biodegradable polymeric scaffolds prepared by thermally induced phase separation", *J. Biomed. Mater. Res.* 1999 47:8–17.

McClellan et. al., "Separating Polymer Solutions Using High Pressure Lower Critical Solution Temperature (LCST) Phenomena", *Polym. Eng. Sci.* 1985 25(17):1088–1092.

Nunes S., "Recent Advances in the Controlled Formation of Pores in Membranes" *TRIP* 1997 5(6):187–192.

*CRC Handbook of Chemistry and Physics*, $72^{nd}$ Ed., CRC Press, USA, 1991 p. 6–4.

* cited by examiner

*Primary Examiner*—Ana Fortuna
(74) *Attorney, Agent, or Firm*—Licata & Tyrrell P.C.

(57) ABSTRACT

Methods for producing open-pore polymeric matrices prepared via gas induced phase inversion are provided. Matrices produced by these methods for various uses including medical implant devices, filtration/separation aids, and porous supports are also provided.

5 Claims, No Drawings

POROUS CONSTRUCTS FABRICATED BY GAS INDUCED PHASE INVERSION

INTRODUCTION

This application claims the benefit of priority from U.S. Provisional Application Serial No. 60/198,026, filed Apr. 18, 2000.

FIELD OF THE INVENTION

The present invention relates to a process for fabricating open-pore polymeric matrices using gas induced phase inversion. The present invention also relates to matrices prepared via this process of varying thickness and shape with open-pore morphologies, and pore sizes and densities ranging from, but not limited, about 10–500 $\mu$m in diameter and about 0.1 to 0.3 g/cm$^3$. In the case of biodegradable and biocompatible polymers, matrices prepared via this process with these characteristics are useful in tissue engineering/regeneration applications including, but not limited to, medical implant devices to promote bone healing, cartilage repair, cellular infiltration and tissue ingrowth. Constructs prepared from commodity, engineering, or other thermoplastic polymers may be useful for such applications as filtration and separation aids and porous supports.

BACKGROUND OF THE INVENTION

A variety of techniques have been developed for fabricating open pore biodegradable polymer scaffolds for tissue engineering applications. The most common methods have been adapted from the polymer membrane industry and include such techniques as phase separation of polymer solutions induced either by thermal instability (Nam et al. J. Biomed. Mater. Res. 1999 47:8–18) or solvent (solubility) instabilities (Nunes, S. TRIP 1997 5(6):187–192; Cohen, J. et. al. Polymer Bulletin 1999 42:345–352), and particulate leaching (Freed et al. J. Biomed. Mater. Res. 193 27:11–23).

Porous polymer constructs produced using thermally induced phase separation (TIPS) have open-pore structures; however, the pore size is typically limited to approximately 10 to 20 $\mu$m in diameter. Recently, porous devices with larger pore sizes and morphologies different from the typical ladder-like structures have been fabricated using TIPS as described in Nam et al. J. Biomed. Mater. Res. 1999 47:8–18, which is incorporated herein by reference. This was achieved by varying the quench depth and the coarsening times for morphology development.

Larger pores can be generated using solvent induced phase separation (SIPS), but asymmetric membranes with a dense skin layer are generally produced. Membranes fabricated by the SIPS technique are cast on a fabric support since the membranes themselves are only a few hundred microns thick. Typically, the membranes will have an asymmetric pore distribution and in some instances, finger like structures are produced. One of the disadvantages associated with SIPS processes is the cost of solvents and their disposal or purification.

A modified SIPS technique can also be applied in the fabrication of thicker and larger porous constructs of varying shape. However, development times required to produce these constructs are on the order of days to weeks. In the case of biodegradable polymers, long development times can be detrimental to the structural integrity of the construct as premature degradation can occur.

In order to achieve sufficient porosity and interconnectivity using leaching techniques, high poragen contents are required. This high poragen loading often leads to mechanically fragile matrices. In the case of low poragen loadings, complete removal of the poragen can be complicated by the presence of closed pores.

Recent efforts have been made in adapting microcellular foaming techniques to produce foams with open pore architecture. Typically, microcellular foaming processes yield closed-cell foams that have pores on the order of about 10 $\mu$m and a pore density of >10$^8$ pores/cm$^3$. In order to generate sufficient interconnectivity, biodegradable polymer compression molded with NaCl particles have been foamed using CO$_2$ microcellular techniques (Harris et. al., Biomed. Mater. Res. 1998 42:396–402). Once foamed, the salt is leached out to create the interconnected pores.

Various methods for production of microcellular foams via the use of supercritical fluid antisolvents (or nonsolvents) have been described. See, for example, U.S. Pat. No. 5,066,684, U.S. Pat. No. 5,116,883, and U.S. Pat. No. 5,158,986. Use of supercritical fluid antisolvents has also been described for production of small particles and coatings of medicaments (U.S. Pat. No. 5,833,891), aerogels (U.S. Pat. No. 5,864,923), membranes (Matsuyama et al. J. of Appl. Polymer Sci. 1999 74:171–178), and in recrystallization of solid materials such as RDX, the explosive cyclotrimethylenetrinitramine (U.S. Pat. No. 5,360,478 and U.S. Pat. No. 5,389,263).

U.S. Pat. No. 5,422,377 discloses a process for producing thin microporous polymeric films for numerous uses including high energy physics targets, biomedical structures for tissue ingrowth, filters, low dielectric films for electronic devices, and asymmetric membranes. In this process, a polymer solution film, comprised of polymer dissolved in a non-volatile solvent, is subjected to a dense or pressurized gas that is not a solvent for the polymer but is soluble in the solvent. The dense gas diffuses into the film, and since the dense gas is soluble in the solvent of the film, but is a non-solvent for the polymer, phase separation occurs and two phases are formed. Simultaneous with the dense gas diffusing into the film is the diffusion of the solvent from the film out into the dense gas. Eventually little solvent remains in the film and the polymer will either glass or crystallize so that the phase separated morphology is locked in. When the pressure of the system is released, the dense gas leaves the film taking with it any remaining solvent while leaving behind a dry microporous polymer film with a cell morphology dependent upon the relationship that existed between the first and second phase.

Many studies have been performed to separate polymers from solution using a supercritical fluid (SCF; Gucke, T. et. al. U.S. Pat. No. 4946940; Mc Clellan A. et. al. Polym. Eng. Sci. 1985 25(17):1088–1092) but their emphasis has mainly been to purify the polymer. Kojima, J. et. al. (Macromol. 1999 32:1809–1815) have examined the early stages of spinodal decomposition in polymer solution under high pressure using light scattering techniques. Poly(vinylidene fluoride) membranes have been synthesized by using water vapor to induce nonsolvent phase separation (Matsuyama H. et. al. J. Appl. Polym. Sci. 1999 74:171–178).

Fabricating matrices which can be varied in thickness, shape and size, and contain interconnected pores of sufficient size, to be useful for the tissue engineering and medical device industries has been problematic.

SUMMARY OF THE INVENTION

An object of the present invention is to provide a method for producing open-pore polymeric matrices which comprises preparing a homogeneous polymer solution comprising one or more polymers and one or more solvents; treating the solution with a gas or supercritical fluid under selected conditions of pressure and temperature so that the gas or supercritical fluid is a nonsolvent or is sparingly soluble for the polymer; allowing the polymer solution to phase separate so that the polymer gels and precipitates from the solution, thus solidifying to form the matrix; if necessary, lowering the temperature of the solution to prevent the polymer from redissolving and help lock-in the pore morphology; and removing the residual solvent preferably via lyophilization. Typically the temperature is lowered near or below the freezing temperature of the solvent or near or below the plasticized glass transition temperature of the polymer/solvent/gas system so that further changes in morphology are minimized upon depressurization.

Another object of the present invention is to provide open-pore polymer matrices prepared via this process of gas induced phase inversion.

Yet another object of the present invention is to provide devices comprising open-pore polymer matrices prepared via this process. Devices which can be prepared include, but are not limited to, medical implant devices comprising open-pore biodegradable matrices and filtration/separation aids and porous supports from commodity, engineering and other thermoplastic polymers.

DETAILED DESCRIPTION OF THE INVENTION

The present invention relates to a new process and open-pore polymer matrices prepared via this process. The process of the present invention offers several advantages over conventional methods for preparation of open-pore constructs by phase inversion techniques such as thermally induced phase separation (TIPS) and solvent induced phase separation (SIPS). Specifically, constructs produced via this process have open pore morphologies with pore sizes and densities ranging from, but not limited to, about 10–500 μm in diameter and about 0.1 to 0.3 g/cm$^3$, depending on the conditions used. The constructs can be fabricated into any shape and desired size and have open-pore surfaces and uniform pore morphologies that are easily controlled by varying process conditions to tailor specific applications. Replacing the traditional liquid non-solvent with a gas or supercritical fluid in the process of the present invention significantly reduces the amount of nonsolvent required in comparison to SIPS techniques, thereby reducing the costs associated with disposal or recycling. The development time of these constructs as compared to the modified SIPS technique for thicker devices is reduced from several weeks to a few days, thereby shortening the time the polymer is in contact with solvents or nonsolvents.

In this process, a polymer solution is prepared. The solution comprises one or more solvents and one or more polymers. In one embodiment of the invention, the polymer solution comprises approximately 10–25 wt % polymer such as poly(desaminotyrosyltyrosine[ethyl ester] carbonate) (p(DTE-co-0% DT carbonate)), or a copolymer such as poly(desaminotyrosyltyrosine [ethyl ester] carbonate-co-desaminotyrosyltyrosine carbonate) (poly(DTE-co-X%DT carbonate), where X % can range from approximately 1 to 100 percent with the appropriate corresponding decrease in DTE composition) in a solvent such as 1,4-dioxane or N-methyl-2-pyrrolidone or mixtures of 1,4-dioxane or N-methyl-2-pyrrolidone with water or tetrahydrofuran (THF). The polymer solution is then poured into a container or mold that is open to a gas or supercritical fluid. Suitable containers include, but are not limited to petri dishes, aluminum pans, glass vials, plastic containers and gas permeable membranes, such as dialysis membranes. The solution is then treated with a gas such as carbon dioxide ($CO_2$) or a supercritical fluid (SCF) under pressure and temperature conditions in which the gas or supercritical fluid is a nonsolvent or is sparingly soluble for the polymer.

For example, a 10–25 wt % polymer solution such as p(DTE-co-0% DT carbonate) or poly(DTE-co-X % DT carbonate) dissolved in 1,4-dioxane is preferably treated with $CO_2$ at room temperature for a prescribed time period sufficient for the gas to diffuse into the polymer solution, resulting in a phase separated system. During phase separation the polymer in the solution gels and precipitates, thereby solidifying to form the matrix. However, the polymer-rich phase at this point is still imbued with solvent and if the pressure is released, the polymer will redissolve. Hence, after the polymer solution has been treated with $CO_2$, the system is cooled to about 0° C. for a prescribed time period to fix or lock-in the pore morphology and minimize further changes to the matrix during depressurization. The $CO_2$ is then released, and the samples are removed from the pressure vessel. The samples are kept cold to prevent the solvent from melting and/or dissolving the polymer. The remaining solvent is then removed from the porous devices preferably via lyophilization.

As will be obvious to those of skill in the art upon this disclosure, however, other polymers at various concentration ranges, other solvents and gases or supercritical fluids, and other conditions including saturation temperatures, times and pressures, and cooling times and temperatures, than those exemplified by this embodiment can be used in this process. Additional exemplary polymers which can be used in this process include, but are not limited to, polyolefins such as polyethylene and polypropylene, polymethacrylates such as polymer(methyl acrylate) and poly(hydroxy ethyl methacrylate), polycarbonates such as poly(bis-phenol A carbonate), styrenic polymers such as polystyrene, block copolymers such as styrene-ethylene-butylene-styrene, vinyl based polymers such as poly(vinyl chloride), polysulfones such as polysulfone and poly(ether sulfone), and polyesters such as poly(ethylene terephthalate). Further, polymers used in these matrices can be modified by attachment of molecules which enhance the utility of the matrix. For example, in one embodiment, wherein the matrix is used as a medical implant, the polymer can be modified to include a molecule which enhances cell attachment or cell growth. In another embodiment, wherein the matrix is used in filtration, the material can be made more hydrophilic or hydrophobic depending upon the application and need for easy wetting of the porous construct. In a preferred embodiment, the polymer comprises poly(DTE-co-1% DT carbonate), poly(DTE-co-X % DT carbonate) where X ranges from about 1 to about 100%, poly(DTE-co-X % DT carbonate) where X ranges from about 1 to about 100% onto which an RGD containing peptide or mimetic thereof is attached, poly(methyl methacrylate), polystyrene, poly (glycolic acid), poly(lactic acid), or copolymers of glycolic and lactic acid. However, it is believed that any polymer/solvent/gas or SCF system can be used in this process provided that the starting conditions and final conditions fall within the ranges required for spinodal decomposition. Further, homogeneous polymer solution phase separates if the two phases are more thermodynamically stable as two separate phases. As demixing occurs, polymer-rich and solvent-rich phases are created. If the homogenous polymer solution is taken from one phase state (above the binodal line) to a condition between the binodal and spinodal line, the polymer solution phase separates by a nucleation and growth type mechanism. This results in formation of individual droplets and a closed pore-type morphology. If the system is taken from one phase state to a point below the spinodal line, phase separation occurs via a spinodal mechanism and leads to the formation of an interconnected, continuous type morphology. Further, a cooling step is not always required. For example, if the phase separated system is stable upon depressurization or if the saturation temperature is sufficiently low, cooling is unnecessary.

Thus, various polymers (degradable and non-degradable), polymer concentrations, solvents and gases and/or supercritical fluids can be selected and used in the process of the present invention. Selection of the polymer is based upon its solubility in the selected solvent and its insolubility in the selected gas/SCF under the conditions used. Concentration of the polymer is selected in accordance with the desired final density of the matrix. When higher concentrations of polymer are used or a different polymer/solvent system is used, it may be necessary to raise the saturation temperature at which the polymer solution is treated with the gas or supercritical fluid so that the polymer solution is homogeneous and does not precipitate from solution before contact with the gas or SCF. Selection of the solvent is based upon its ability to dissolve the selected polymer. Preferred solvents have a freezing point between approximately −40° C. and 15° C. so that the pore morphology of the matrix can be locked in and further changes minimized upon depressurization by lowering the temperature of the system below or near the freezing point of the solvent, or below or near the plasticized glass transition temperature of the polymer/solvent/gas system. When polymers are swollen with solvent or contain dissolved gases, transition temperatures may be depressed (Chiou J. et. al. J. Appl. Polym. Sci. 1985 30:2633–2642), thus allowing them to flow at much reduced temperatures than would otherwise be expected. The glass transition temperature is the temperature at which an amorphous or partially amorphous polymer crosses from a rigid glassy state to one that is capable of flowing. Preferred solvents also have a moderate boiling point so that the solvent can be easily removed to fix the pore morphology and minimize further changes to the matrix. It should be noted that a cooling step is not always required to fix the pore morphology and minimize further changes to the matrix. For example, if the phase separated system is stable upon depressurization or if the saturation temperature is sufficiently low cooling is not required.

Using combinations of solvents is another technique of changing the morphology of the constructs. The addition of a nonsolvent to the polymer will effect the kinetics and pathways of phase separation, leading to different structures in the final device. Similarly, combinations of gases and blends of polymer can also be employed.

Selected gases and supercritical fluids used in this method must have relatively low solubilities in the selected polymer under the conditions of temperature and pressure to be used. A preferred gas is $CO_2$. However, supercritical fluids (SCF) such as supercritical $CO_2$ can also be used. The solvent power of $CO_2$ is dependent on its density. Thus, using $CO_2$ in the SCF state will have effects on the phase inversion process depending on the temperature and pressure of the system, as SCF $CO_2$ is a tunable solvent. The selected gas plays a major role in pore morphology development.

The most commonly used supercritical fluid (SCF) solvents exist as liquids or gases at ambient pressures and temperatures. When compressed and heated to conditions above their critical points, these compounds become supercritical and have densities and transport properties that are intermediate between their liquid and gaseous states. Once a compound is at a temperature and pressure greater than its critical point, it exists as one phase no matter how much it is compressed. The critical point for $CO_2$ is 31.1° C. and 7.37 MPa. The solvent capacity of SCF $CO_2$ is density dependent and, thus, can be controlled by changing the temperature and pressure to vary the solvent power between that of a gas and liquid. This property is what makes a SCF a tunable solvent, a characteristic that is not available with traditional liquid solvents. The critical properties of a series of compounds commonly used as SCF solvents are listed in Table 1.

TABLE 1

Critical Parameters of Compounds Commonly Used in SCF Processes

| Compound | Formula | $T_c$ (° C). | $P_c$ (MPa) | $\rho_c$ (g/cm³) |
|---|---|---|---|---|
| Carbon Dioxide | $CO_2$ | 31.0 | 7.37 | 0.47 |
| Nitrous Oxide | $N_2O$ | 36.5 | 7.26 | 0.46 |
| Freon 22 | $CHClF_2$ | 96.1 | 4.98 | 0.24 |
| Sulphur Hexafluoride | $SF_6$ | 45.6 | 3.82 | 0.69 |
| Nitrogen | $N_2$ | −146.9 | 3.45 | 0.30 |
| Methane | $CH_4$ | −82.3 | 4.71 | 0.16 |
| Ethane | $C_2H_6$ | 32.2 | 4.89 | 0.19 |
| Propane | $C_3H_8$ | 96.8 | 4.27 | 0.20 |
| Ethylene | $C_2H_4$ | 9.9 | 50.5 | 0.22 |
| Propene | $C_3H_6$ | 91.9 | 45.4 | 0.24 |
| Water | $H_2O$ | 374.2 | 22.1 | 0.24 |
| Methanol | $CH_3OH$ | 239.4 | 8.02 | 0.20 |
| Hexane | $C_4H_{14}$ | 234.5 | 3.03 | 0.20 |

A series of samples were prepared in accordance with the process of the present invention. For these samples, a 20 wt % poly(DTE-co-0% DT carbonate) solution in 90:10 dioxane:water was treated with $CO_2$. When the same solution was cooled to 0° C. but not exposed to $CO_2$, it did not freeze or solidify. However, when cooled to about −15° C., the polymer and solvent of the untreated solution did phase separate by thermally induced phase separation (TIPS). The resulting morphology of this device was significantly different from the device prepared in accordance with the present invention. The device prepared in accordance with the process of the present invention has large rounded pores, on the order of about 100 to 150 μm, which are interconnected. The pore walls are smooth and there are several interconnecting holes in the walls. In contrast, the device prepared by simply cooling the polymer solution to −15° C. has pores on the order of about 10–15 μm. These pores are arranged such that they resemble a series of parallel ladders-typical of the structure formed by TIPS.

Examination of various matrices prepared via the process of the present invention revealed that 20 wt % poly(DTE-co-0% DT carbonate) in 90:10 dioxane water produced a very homogeneous matrix. Strong visual evidence of pore interconnectivity was also observed by scanning electron microscopy (SEM). Pore interconnectivity was confirmed by mercury porosimetry analyses.

The sample described in the preceding paragraphs was prepared inside of a pressure vessel, and it was uncertain as to when or how phase inversion actually occurred.

Accordingly, a critical point drying apparatus (CPDA) was modified such that the phase inversion process of the present invention could be observed. In addition, the CPDA permits screening of potential candidates for this process and determination of the operating window for phase inversion. Any pressure vessel equipped with a viewing window would suffice for this purpose.

The CPDA used in these experiments comprises a pressure chamber along with a series of valves, a glass window, pressure and temperature gauges, and a thermostat jacket. The diameter of the pressure vessel is 1 inch and the length of the barrel is 3 inches. The pressure rating is 1800 psi. Polymer solution or solvent/solvent mixtures were poured into glass vials (8 mm inner diameter×15 mm) filled approximately ⅓ to ⅔ full. Graduated stickers were placed on the vials to aid in monitoring changes in the system during the phase inversion process. A maximum of three sample vials were attached at the end of a glass microscope slide and inserted into the CPDA. The $CO_2$ pressure applied on the system was slowly raised and the phase inversion process monitored.

In general, when the solutions were brought into contact with $CO_2$, the liquid-gas interface became turbulent. As $CO_2$ dissolved into the solutions, their volumes expanded and the system pressure decreased. Eventually, a $CO_2$ rich front developed and moved down through the solution. When the dissolved $CO_2$ concentration surpassed a critical level, the polymer solutions began to phase separate. The surface in contact with the $CO_2$ precipitated from solution first. A small increase in the construct height is observed due to the sorption of $CO_2$ into the polymer solution before the polymer precipitates from solution. Once the first solid layer of polymer formed, the relative change in height was negligible. As the process continued, a layer of solvent was deposited on top of the phase separated polymer. The fact that the top surface is porous allows the flow of solvent out as more $CO_2$ is dissolved into the solution. Thus, the process of the present invention is different from the process disclosed in U.S. Pat. No. 5,422,377 as the porous construct is not dry after depressurization. Instead, the residual solvent is removed by lyophilization. In the process of the instant invention, the amount of solvent that has to be lyophilized can be reduced by adding more polymer solution such that it occupies most of the volume of the container. As the $CO_2$ sorbs into the polymer, the aliquot of solvent that is displaced by the sorption of $CO_2$ would spill over the top. There would, however, still be some solvent remaining in the pores and in the bulk of the material.

The CPDA can also be used to observe methods for controlling the pore size in this process through varying of the polymer concentration, changing the solvent or adding a cosolvent/nonsolvent, varying the pressure, changing the temperature, using different gases and/or supercritical fluids or a mixture thereof, and pre-conditioning the polymer solution so that the solution expands but the polymer does not precipitate from solution followed by an increase in the pressure to induce phase inversion.

Some of the samples were made from different lots of polymer. Though the chemical composition is the same, their molecular weights are different. This may lead to some of the variation in pore size for matrices made using similar conditions as the solvent viscosities may vary resulting in slightly different $CO_2$ diffusion rates, thus influencing the kinetics of phase separation.

Characteristics of the porous polymer matrices prepared via the process of the present invention are within the range considered to render them useful as medical implants for bone and cartilage repair. More specifically, biodegradable devices can be prepared via the process of the present invention with pore sizes ranging from about 10 to about 500 $\mu$m, more preferably about 100 to about 250 $\mu$M, in diameter and open porosities in the range of about 90% to about 100%, more preferably about 100%.

Further, porous constructs can be prepared via the process of the present invention in approximately 1 to 3 days depending on the polymer/solvent/gas system and thickness of the device.

Thus, an advantage of the process of the present invention is that it minimizes the time the polymer is in contact with solvents. This new process is also adaptable to other polymers including, but not limited to PS and PMMA, as well as other solvents and gases. Temperature and pressure conditions for processing matrices from various polymers, solvents and gases are selected in accordance with the phase diagram of the system. As demonstrated herein, this process also allows for variations in pore morphology of matrices depending upon selected uses via changes in polymer concentration, solvent ratio and pressure without affecting pore size.

This technique can also be used to coat other biomedical implants, such as metal implants which require close bone apposition. The fact that the surface of the constructs prepared via the method of the present invention are open pore allows for cell ingrowth into the coating/matrix which provides a temporary scaffold for bone to regenerate, thus allowing for a more spatially defined growth.

Matrices prepared in accordance with this process from commodity, engineering and other thermoplastic polymers are also useful as filtration/separation aids and porous supports.

EXAMPLES

The following nonlimiting examples are provided to further illustrate the present invention.

Example 1

Preparation of Poly(DTE-co-0% DT Carbonate) in 1,4-Dioxane

Matrices were prepared via the process of the present invention from polymer solutions comprising 15, 20 and 25 wt/vol % poly(DTE-co-0% DT carbonate) in 1,4-dioxane. The polymer solutions were poured into open containers (Al dishes) and placed inside a pressure vessel, which was then filled with 650 psi $CO_2$ at room temperature. There was an initial drop in pressure due to the dissolution of gas in the polymer solution. Accordingly, the pressure did not stay at 650 psi, but rather continued to decrease until an equilibrium condition was reached. At this point, the pressure remained constant. Eighteen hours later and still under pressure, the system was cooled to about 0° C. for three hours. The $CO_2$ was slowly released, and the samples removed from the pressure vessel. A significant amount of solvent (dioxane and water) extracted from the polymer solution was found on top of the polymer. The sample was lyophilized to remove residual solvent from the porous construct.

The morphologies of the porous constructs prepared in this fashion were analyzed by scanning electron microscopy (SEM). SEM is a technique whereby a scanning electron microscope is employed to visualize an appropriately prepared sample for visualization of, for instance, architecture, morphology, pore sizes and shapes. SEM images showed that the surface exposed to the $CO_2$ is open pore. The surface contains a mixture of large pores (diameters similar to the bulk regions) and smaller pores as observed on the pore walls. The fact that the surface is not exclusive is expected to be beneficial for biomedical applications where cell infiltration is desirable. The effect of increasing the polymer concentration from 15, 20, to 25 wt % poly(DTE-co-0% DT carbonate), was to decrease the pore size from about 81, about 52, to about 28 µm, respectively, as determined visually by SEM, and to increase the matrix density.

Example 2

Variations in Solvent

Polymer constructs prepared by dissolving poly(DTE-co-0% DT carbonate) in 1,4-dioxane and in a 90:10 mixture of 1,4-dioxane:water at 20 wt/vol % were compared. The polymer 5 solutions were exposed to 650 psi $CO_2$ at room temperature for 18 hours. The system was then cooled to about 0° C. for 3 hours and the pressure released. Samples were kept cold and the residual solvent was removed by lyophilization.

The addition of water, a non-solvent for poly(DTE-co-0% DT carbonate), to the solution increased the pore size from 52 to 140 µm. Under visual examination by SEM, the matrix appeared to be much more open when 10 vol % of water was added to the dioxane. The pore walls contained a greater number of interconnecting pores.

Example 3

Variations in Pressure

Since the solvent power of $CO_2$ is dependent upon its density, the pore size and architecture can also be varied by changing the pressure and temperature of the $CO_2$. Using 15 and 20 wt % poly(DTE-co-0% DT carbonate) in 1,4-dioxane solutions, the effect of $CO_2$ pressure on the pore morphology was examined. Poly(DTE-co-0% DT carbonate) solutions were poured into petri dishes and treated with 500 and 650 psi $CO_2$ in the pressure vessel. After being treated with $CO_2$ for 18 hours, the system was cooled to about 0° C. for 3 hours. The $CO_2$ was released slowly, and the samples were removed from the pressure vessel. Samples were kept cold and lyophilized to remove solvent from the porous devices.

Samples prepared with 15 wt % poly(DTE-co-0% DT carbonate) appeared to have larger pores than the sample prepared with 20 wt % poly(DTE-co-0% DT carbonate) as determined by SEM. The average pore size increased when the polymer solutions were treated with 500 psi $CO_2$ rather than at 650 psi $CO_2$.

The effect of $CO_2$ pressure on the morphology was examined in additional experiments using 20 wt % poly (DTE-co-0% DT carbonate) in 1,4-dioxane solutions. Poly (DTE-co-0% DT carbonate) solutions were poured into petri dishes and treated with $CO_2$ at pressures ranging from 500 to 800 psi in the pressure vessel. After being exposed to $CO_2$ for 18 hours, the system was cooled to 0° C. for 3 hours. The $CO_2$ was then released slowly, and the samples were removed from the pressure vessel. The samples were kept cold and lyophilized to remove the solvent from the porous devices.

Samples prepared at the lower pressures had larger pore sizes as determined by SEM. The average pore sizes were about 101, about 42 and about 17 µm for the matrices prepared at 500, 650 and 850 psi, respectively. For the samples prepared at 850 psi the pressure was readjusted after the initial drop in pressure, and a bimodal distribution of pore sizes was observed. The larger pores, 1 mm in diameter, were sporadically found and were interconnected with the smaller pores which occupied the bulk of the device. Thus, overall the average pore size decreased as the pressure was increased.

Example 4

Variations in Polymer Composition

Porous constructs were fabricated from a homologous series of poly(DTE-co-X % DT carbonates) with DT contents ranging from 0% to 50% DT. Again, 20 wt/vol % polymer solutions were prepared in 90:10 dioxane:water. The polymer solutions were exposed to 650 psi $CO_2$ at room temperature for 18 hours. The system was then cooled to about 0° C. for 3 hours and the pressure released. Samples were kept cold and the residual solvent was removed by lyophilization.

Pore sizes of matrices prepared from poly(DTE-co-50% DT carbonate) were significantly smaller as compared to matrices prepared from poly(DTE-co-0% DT carbonate). It was found that pore size decreased from approximately 140 to about 64 µm when the DT content was increased from 0 to 50%. This difference in pore size is attributable to variation in the relative solubility characteristics of the different components as the DT content is varied. Table 2 shows properties, including pore size, of matrices prepared with various concentrations of DT.

TABLE 2

Properties of porous poly (DTE-co-X% DT carbonate) Constructs

| DT Content | Average Pore diameter (µm) | Density (g/cm³) | % Open porosity |
|---|---|---|---|
| 0% | 137 | 0.21 | 93 |
| 10% | 158 | 0.16 | 100 |
| 20% | 86 | 0.19 | 100 |
| 30% | 82 | 0.24 | not measured |
| 40% | 81 | 0.22 | not measured |
| 50% | 64 | 0.21 | 97 |

Example 5

Poly(methylmethacrylate) and Polystyrene Constructs

Porous constructs were fabricated from poly(methyl methacrylate) (PMMA) and from polystyrene (PS). The PMMA was dissolved at 20 wt/vol % in 90:10 dioxane:water, and the PS dissolved in pure dioxane at 20 wt/vol %. The polymer solutions were exposed to 800 psi $CO_2$ at room temperature for 18 hours. The system was then cooled to about 0° C. for 3 hours and the pressure released. Samples were kept cold and the residual solvent was removed by lyophilization.

The PMMA sample construct was very homogeneous, having an average pore size of about 30 µm and an open porosity as determined by porosimetry of 100%. The solution was cast in an Al dish and the construct had pulled away from the dish, hence resulting in a matrix with a density of about 0.29 g/cm³. The PS construct had pore sizes on the order of about 500 to about 700 µm in diameter and was not as uniform as the PMMA matrix. The surface was coarse and appeared to have collapsed in some regions. It is believed that a higher pressure, a lower temperature, or the use of a different solvent(s), may stabilize the matrix during the phase inversion process.

Example 6

RGD Modified Poly(DTE-co-25% DT Carbonate) Construct

An arginine-glycine-aspartic acid (RGD) (Gante, J. Angew. Chem. Int. Ed. Engl. 1994 33:1699–1720; Haubner et. al. J. Am. Chem. Soc. 1996 118:7881–7891; Craig, W. Biopolymer (Peptide Science) 1995 37:157–175) peptide modified poly(DTE-co-25% DT carbonate) was also fabricated into a porous construct via the method of the present invention using a 20 wt % polymer solution in 90:10 dioxane:water exposed to 630 psi $CO_2$ at room temperature for 18 hours. The system was then cooled to about 0° C. for 3 hours and the pressure released. Samples were kept cold and the residual solvent was removed by lyophilization. The interconnected morphology of this construct resembled a poly(DTE-co-0% DT carbonate) sample rather than a poly(DTE-co-25% DT carbonate) which contains a large number of smaller interconnection points. When peptides are attached to the polymer pendent functionalities, the number of free carboxyl groups on the polymer is reduced. This is expected to influence the mutual solubilities of the polymer, $CO_2$ and solvents, hence affecting the phase inversion process. The presence of the peptide also effects solubility of the polymer.

Example 7

Inducing Freeze Patterns

Constructs fabricated from 20 wt/vol % solution of poly(DTE-co-5% DT carbonate) in 90:10 dioxane:water exhibited a freeze pattern along with the round open pore morphology. The surface of the round pores was marred by the presence of ladder-like structures. This freeze pattern is believed to be due to residual solvent in the bulk material following the polymerization step which is capable of swelling the polymer and which freezes during the cooling or $CO_2$ release step. Upon drying the poly(DTE-co-5% DT carbonate) before the process of the instant invention, the pore morphology did not show evidence of freezing. Thus, a freeze pattern can be induced by freezing a partially precipitated or gelled phase separated solution to solidify the matrix. This technique introduces surface roughness into the porous constructs.

Example 8

Variations in Molds

Samples were also prepared in various containers to determine the effects of the various molds. Poly(DTE-co-0% DT carbonate) solutions in 90:10 dioxane:water were prepared at 20 wt/vol % and cast into glass vials, Al dishes, glass petri dishes and Teflon petri dishes and molds.

No visual differences in morphology were observed between samples cast in the Al pan and the glass petri dish or glass vial. However, the Al pan can be easily peeled off the back of the matrix making it easier to remove the sample. SEM analysis of biopsy punches of these samples revealed open pores on the surface and edges of the punch. Accordingly, porous architecture was not damaged from punching (cutting) the sample.

Samples prepared in Teflon retained the shape of their molds; however, the devices were smaller. The polymer solution does not wet the Teflon surface, thus allowing $CO_2$ to diffuse between the mold wall and solution. Also, the polymer, as it precipitates from solution, does not adhere to the sides of the Teflon mold, but rather shrinks away from the surface. This reduction in size effects the overall density of the device.

Example 9

Modifying Pore Morphology

The ability to modify pore morphology of matrices without changing pore size via variation of conditions used in the process of the present invention was demonstrated. In initial experiments, two samples were prepared from poly(DTE-co-25% DT carbonate) using two different solvent ratios of dioxane and water at two different pressures. Specifically, a first sample was prepared from a 20 wt % poly(DTE-co-25% DT carbonate) solution in 90:10 dioxane:water at about 650 psi. A second sample was prepared from a 20 wt % solution in 95:5 dioxane:water at about 750–800 psi. The morphologies produced were strikingly different, however, the average pore size remained about, the same. The construct fabricated from the 90:10 dioxane:water solution had an average pore size of approximately 55 to 75 $\mu$m, thicker pore walls with smaller interconnecting pores are on the order of about 10 $\mu$m in diameter. The sample prepared from the 95:5 dioxane:water solution also has pores in the range of about 65 to about 85 $\mu$m; however, its pore walls appear to be much thinner with many smaller interconnecting pores that were about 1–2 $\mu$m in diameter.

TABLE 3

Properties of Porous Poly (DTE-co-25% DT carbonate) Constructs

| Phase | 1,4- | P (psi) | Average | Density | % Open |
| --- | --- | --- | --- | --- | --- |
| $CO_2$ | 90:10 | 650 psi | 65 | 0.21 | 99 |
| $CO_2$ | 95:5 | 800 psi | 77 | 0.17 | 89 |
| TIPS | 90:10 | −18° C. | 20 | 0.21 | 100 |
| TIPS | 95:5 | −18° C. | 16 | 0.26 | 99 |

The above matrices were implanted subcutaneously in rats and showed good cell infiltration. Hence, these devices have pores with sufficient interconnectivity to allow for cell ingrowth.

Example 10

Incubation/Degradation Effects

Porous constructs were fabricated from a homologous series of poly(DTE-co-DT carbonates) with DT contents ranging from 0% to 40%. Again, 20 wt/vol % polymer solutions were prepared in 90:10 dioxane:water. The polymer solutions were exposed to 650 p $CO_2$ at room temperature for 18 hours. The system was then cooled to about 0° C. for 3 hours and the pressure released. Samples were kept cold and the residual solvent was removed by lyophilization.

As the DT content increases, materials also become increasingly hydrophilic and anionic in nature, and more susceptible to hydrolytic degradation (Brode et al. ACS Polymer Preprints 1998 39:230–231; incorporated herein by reference). After 24 hours of incubation in PBS at 37° C., matrices prepared by the process of the present invention from poly(DTE-co-30% DT carbonate) and poly(DTE-co-40% DT carbonate) showed some evidence of surface erosion. The pH of the PBS decreased to 6.7 and 6.2, respectively, for poly(DTE-co-30% DT carbonate) and poly(DTE-co-40% DT carbonate), and was hazy, indicating that degradation of the polymers had occurred.

The results from the compressive study revealed that the mechanical properties of the porous constructs are greatly influenced by incubation/degradation. This trend has been observed previously for poly(DTE-co-0% DT carbonate) fibers (Bourke et al. Soc. Biomater. 25th Ann. Mtg. Trans. 1999 XXII:222). The compressive strength retention after 24 hours was less than 50% for poly(DTE-co-30% DT carbonate) and poly(DTE-co-40% DT carbonate), whereas there was a slight increase in strength for poly(DTE-co-0% DT carbonate) and poly(DTE-co-25% DT carbonate).

The ability to control resorption time and pore morphology of matrices for tissue engineering and regeneration are essential in many situations. The process of this invention, along with a homologous series of biodegradable polymers, such as poly(DTE-co-X% DT carbonate), provides a method of tailoring porous biodegradable devices for different applications.

Example 11

Use in Tissue Engineering

The ability of matrices produced by the process of the present invention to be used as tissue engineering devices was examined. Cell attachment studies were first conducted on fractured surfaces of poly(DTE-co-0% DT carbonate) and poly((DTE-co-25% DT carbonate) using MG63 cells (an osteosarcoma cell line typically used for cell attachment studies) in the presence of serum. Cells were allowed to attach for approximately 90 minutes at 37° C. Results from these studies indicated that a higher DT content, to some critical level, may be more favorable for initial cell attachment. A few cells were found sporadically on the poly(DTE-co-0% DT carbonate) surface; whereas, a much greater number of cells were attached to poly(DTE-co-25% DT carbonate) matrix. The cells on the more hydrophobic poly (DTE-co-0% DT carbonate) construct were rounded, and in stark contrast to the cells attached on poly(DTE-co-25% DT carbonate) matrix which for the most part were well spread.

Using longer assay time, about 210 minutes, the effects of increasing the DT content were more pronounced. Cells did attach to the porous poly(DTE-co-0% DT carbonate) samples and signs of cell spreading and migration were observed. As the DT content increased from 5 to 15%, the number of cells attached and the extent to which they were spread were substantially greater. Beyond 15% DT, the effects were similar with the porous constructs being nearly covered with a layer of spread cells.

At the higher DT contents, 30% and above, evidence of surface erosion was found during the time scale of the experiment, namely 210 minutes at 37° C. Significant surface erosion of the poly(DTE-co-50% DT carbonate) matrix was evident and no cells were found attached to the surface at the end of the assay. The pore structure was, however, still present, indicating that the polymer eroded from the surface and not through bulk degradation. A shorter cell attachment assay is required to determine if the cells did initially attach to the poly(DTE-co-50% DT carbonate) matrix and then became detached as the surface eroded. Open-pore matrices prepared by the process of the current invention using poly(DTE-co-X % DT carbonate), having tailored degradation and surface erosion rates, as well as the ability to elicit different matrix/protein/cell interactions, are extremely desirable in such applications as, but not limited to, drug delivery and tissue engineering/regeneration.

In the absence of serum, similar results were obtained though to a lesser extent. A minimal number of rounded cells were found on poly(DTE-co-0% DT carbonate). When the DT content was increased to 10%, the surface of the porous construct contained numerous cells that were mainly rounded or just beginning to take on the spread morphology.

Example 12

Monitoring Phase Inversion

The phase inversion process was monitored via the use of a critical point drying apparatus (CPDA) as the pressure vessel. Two solutions were used in these experiments, a 90:10 dioxane:water mixture (solvent only) and a 20 wt % poly(DTE-co-0% DT carbonate) solution in 90:10 dioxane:water. Images were taken with a digital camera and a time course was plotted.

Some turbulence or swirling patterns at the $CO_2$:polymer solution interface developed immediately. At approximately 400 psi $CO_2$, signs of phase separation were evident in the 20 wt % poly(DTE-co-0% DT carbonate) solution in 90:10 dioxane:water as noted by the appearance of a white band at the top of the polymer solution. The volume of the polymer solution expanded slightly as phase separation proceeded. The turbulence in the dioxane:water ceased after the $CO_2$ pressure on the system had reached the desired fill pressure. Distinct layers developed in the 90:10 dioxane:water solvent mixture, and the diffusion front traversed the length of the vial. The pure solvent dilated more than the polymer solution. One possible reason to account for this phenomenon is that the sorption of $CO_2$ in the polymer is less than in the pure solvent itself, and thus its effect on the volume is reduced.

At about 4 minutes, the $CO_2$ pressure was in the region of 630 psi and approximately a 1 mm layer of poly(DTE-co-0% DT carbonate) had precipitated from solution. After 7 minutes into the process, a layer of solvent developed on top of the precipitated polymer. This liquid was displaced due to the partial molar volume occupied by $CO_2$ dissolved in the polymer and solvents. The precipitated polymer was porous, thus allowing the fluid to expand up and percolate through. Just below the precipitated polymer was a region in which the $CO_2$ concentration was not sufficient for the polymer to solidify but high enough to induce phase separation as evidenced by the increase in opacity. As $CO_2$ continued to diffuse into the solution, the precipitated polymer layer expanded, and the volume of liquid on top of the polymer layer increased. This displaced aliquot of solvent explains the appearance of crystallized solvent on top of the samples after cooling and depressurization.

Once phase inversion was complete, the pressure on the system was reduced to about 380 psi. Almost immediately, the volumes of the solutions decreased. The poly(DTE-co-0% DT carbonate) became more opaque as the concentration of $CO_2$ was insufficient to keep the phase separated polymer fully precipitated. After 18 hours, the polymer was still phase separated; however, the poly(DTE-co-0% DT carbonate) was only partially gelled and still highly swollen, as indicated by its opaqueness. Its structure had rearranged as its volume was condensed. The system pressure was increased again to approximately 630 psi $CO_2$, causing the gelled polymer to turn white and precipitate from solution. The solvent on top of the polymer turned milky. While not wishing to be bound by this explanation, it most likely contained some low molecular weight polymer species.

Example 13

Rate of Phase Inversion with Varying Solvent Concentrations

The rate of phase inversion of poly(DTE-co-0% DT carbonate) solutions of varying concentration in 90:10 dioxane:water was compared. Polymer solutions with concentrations of 5, 10 and 20 wt/vol % were prepared and placed in the CPDA. A pressure of 650 psi $CO_2$ was placed on the system. The rate of precipitation was dependent on the amount of polymer in solution. After achieving 650 psi, the entire volume of the 5 wt/vol % solution had precipitated from solution in under 10 minutes, while the 10 wt/vol % solution was approximately 50% precipitated and the 20 wt/vol % was about 30% precipitated. The viscosity of the polymer solution increases with polymer concentration and, hence, the rate at which $CO_2$ can diffuse into the solution is reduced. With time, the precipitated polymer phase in the 5 wt/vol % continued to evolve though the polymer solution had already under gone phase inversion. Initially, the solution was more uniform; however, driven by thermodynamic forces, the polymer rich phases coalesced to form a more compact layer.

In additional experiments, phase separation of three solutions, 20 wt % PMMA in 90:10 dioxane:water, a mixture of 90:10 dioxane:water, and 20 wt % poly(DTE-co-0% DT carbonate) in 90:10 dioxane:water, was examined in the CPDA. The fill pressure was 630 psi at room temperature.

In these experiments, it was found that the rate of phase inversion for the PMMA solution was slightly faster than in poly(DTE-co-0% DT carbonate) solution; however, the PMMA only partially gelled and was still highly swollen as indicated by it's opaque appearance. In contrast, the poly (DTE-co-0% DT carbonate) had become solid and taken a white appearance. While not wishing to be bound by the following explanations, PMMA absorbs a higher concentration of $CO_2$ than poly(DTE-co-0% DT carbonate) and, hence, a higher concentration of $CO_2$ may be required for phase inversion to occur. Also, the relative solubilities of PMMA and poly(DTE-co-0% DT carbonate) in 90:10 dioxane:water are expected to be quite different.

The system pressure was then increased to about 800 psi $CO_2$ and, as with the poly(DTE-co-0% DT carbonate), the PMMA solidified into a porous white construct. While not wishing to be bound by this explanation, it is believed that this stepwise exposure of the polymer solution to $CO_2$ has an effect on the pore size and morphology of the resulting construct, arising from differences caused by the initial dilation of the polymer solution prior to precipitation. Also, the rate at which the polymer precipitates from solution should be quicker, resulting in different coarsening effects, as there is already an appreciable amount of $CO_2$ dissolved in the PMMA solution.

Phase separation of two solutions, 20 wt % PMMA in 90:10 dioxane:water and 20 wt % poly(DTE-co-0% DT carbonate) in 90:10 NMP:water, was also examined in the CPDA at 800 psi $CO_2$. The rate of $CO_2$ diffusion into the dioxane:water:PMMA system was significantly faster than into NMP:water:poly(DTE-co-0% DT carbonate); as noted by the rate of volume increase due to dissolved $CO_2$. The PMMA phase separated from solution forming a white solid within 3.5 hours. The poly(DTE-co-0% DT carbonate) solution in 90:10 NMP:water exposed to 800 psi $CO_2$ at room temperature formed a highly swollen polymer layer. Small changes in temperature caused this layer to either redissolve or to further precipitate from solution, thus indicating that a lower processing temperature may be required to fabricate a porous construct from this system at 800 psi $CO_2$. The reduction in temperature causes the concentration of dissolved $CO_2$ to increase and the solubility of the polymer to decrease. The sorption of $CO_2$ into the NMP:water system was much slower than in the dioxane:water mixture; also the relative solubility was lower. (See Table 4) This, along with the fact that NMP is a better solvent for poly(DTE-co-0% DT carbonate), may have caused incomplete precipitation of the poly(DTE-co-0% DT carbonate) from solution.

TABLE 4

Solubility data of $CO_2$ in dioxane, NMP and water at 303 K and 1 atmosphere

|  | Dioxane[†] | NMP[†] | Water[‡] |
|---|---|---|---|
| Density (g/cm$^3$) | 1.0279 | 1.0271 | 1.00 |
| Molar Mass (g/mol) | 88.11 | 99.13 | 18.02 |
| Mole Fraction ($X_{CO2}$) | 0.0192 | 0.0138 | 0.000821 |
| g $CO_2$/100 g solvent | 0.978 | 0.621 | 0.201 |

[†]Kassim et. al. Fluid Phase Equilibria 1988 41:287–294
[‡]CRC Handbook of Chemistry and Physics, 72nd Edn, CRC Press, USA, 1991, p. 6–4.

In this experiment, the pressure of the system was released quickly after both solutions had fully precipitated. The 90:10 dioxane:water solution in the PMMA solution bubbled rapidly and eventually froze due to the cooling effect of rapid $CO_2$ release. The partially precipitated poly (DTE-co-0% DT carbonate) in the 90:10 NMP:water began to whiten, indicating that it was becoming less soluble as the temperature decreased. The NMP:water mixture did not bubble significantly, suggesting that the rate of $CO_2$ sorption/desorption is slow and/or $CO_2$ has a low solubility in the solvent mixture. By lowering the saturation temperature, the solubility of $CO_2$ in the polymer and solvents is increased, as well as the tendency for the polymer to precipitate from solution. Lowering the saturation temperature would result in the formation of a porous construct using the NMP:water:poly(DTE-co-0% DT carbonate) system. Alternatively SCF $CO_2$ could be used by raising the temperature and pressure above its critical point (31.05° C. and 1070.82 psi $CO_2$; International Thermodynamic Tables of the Fluid State—Carbon Dioxide, Pergamon Press, NY, 1973) so that higher pressures and hence, increased $CO_2$ solubilities, can be achieved.

What is claimed is:

1. A method for producing an open-pore polymer matrix with pore sizes ranging from 10–500 μm in diameter comprising:
    (a) preparing a homogeneous polymer solution comprising one or more polymers and one or more solvents;
    (b) pouring the solution into an open container or mold for the matrix;
    (c) contacting the solution with a gas or supercritical fluid in a pressure vessel under selected conditions of pressure and temperature such that the gas or supercritical fluid is a nonsolvent for or is sparingly soluble in the polymer;
    (d) allowing the polymer in the solution to phase separate into a polymer gel precipitate and solidify to form the matrix;
    (e) fixing the pore morphology so that further changes to the matrix are minimized;
    (f) depressurizing the pressure vessel and removing the matrix from the pressure vessel; and
    (g) removing residual solvent from the matrix.

2. An open-pore polymer matrix with pore sizes ranging from 10–500 μm in diameter synthesized via the method of claim 1.

3. The open-pore polymer matrix of claim 2 comprising a biodegradable polymer.

4. A medical implant device comprising the open-pore biodegradable polymer matrix of claim 3.

5. A biodegradable polymer coating for medical devices and implants comprising the open-pore biodegradable polymer matrix of claim 3.

* * * * *